(12) United States Patent
Halston et al.

(10) Patent No.: US 6,589,541 B2
(45) Date of Patent: Jul. 8, 2003

(54) SPRAYABLE BEAUTIFYING COMPOSITION

(75) Inventors: Yolanda Halston, Malibu, CA (US); Richard Berg, Perris, CA (US)

(73) Assignee: Classified Cosmetics, Inc., Malibu, CA (US)

( * ) Notice: Subject to any disclaimer, the term of this patent is extended or adjusted under 35 U.S.C. 154(b) by 0 days.

(21) Appl. No.: 09/861,226

(22) Filed: May 18, 2001

(65) Prior Publication Data

US 2002/0172695 A1 Nov. 21, 2002

(51) Int. Cl.$^7$ .......................... A61K 7/42; A61K 7/021; A61K 7/00; A61K 9/00
(52) U.S. Cl. .......................... 424/401; 424/43; 424/59; 424/63; 424/400; 424/47
(58) Field of Search ................................ 424/400, 401, 424/59, 43, 63, 47

(56) References Cited

U.S. PATENT DOCUMENTS

| | | | |
|---|---|---|---|
| 3,812,246 A | 5/1974 | Vanlerberghe et al. | |
| 3,846,546 A | 11/1974 | Lachampt et al. | |
| 4,309,119 A | 1/1982 | Wittersheim | |
| 4,350,605 A | 9/1982 | Hughett | |
| 4,714,084 A | 12/1987 | Berry et al. | |
| 4,742,963 A | 5/1988 | Marvaldi | |
| 5,044,520 A | 9/1991 | Moisan | |
| 5,050,624 A | 9/1991 | Kobe et al. | |
| 5,243,711 A | 9/1993 | Graham | |
| 5,268,166 A | 12/1993 | Barnett et al. | |
| 5,352,437 A | 10/1994 | Nakagawa et al. | |
| 5,429,815 A | 7/1995 | Faryniarz et al. | |
| 5,443,817 A | 8/1995 | Zimmerman et al. | |
| 5,494,674 A | 2/1996 | Barnett et al. | |
| 5,650,146 A | 7/1997 | Shaw | |
| 5,660,839 A | 8/1997 | Allec et al. | |
| 5,662,890 A | 9/1997 | Punto et al. | |
| 5,665,368 A | * 9/1997 | Lentini et al. | 424/401 |
| 5,700,451 A | * 12/1997 | Yue et al. | 423/610 |
| 5,710,141 A | * 1/1998 | Lin et al. | 514/159 |
| 5,747,011 A | * 5/1998 | Ross et al. | 424/400 |
| 5,945,111 A | 8/1999 | Esser | |
| 5,989,529 A | * 11/1999 | Kaplan | 424/400 |
| 6,062,688 A | 5/2000 | Vinas | |
| 6,146,617 A | * 11/2000 | Kurz et al. | 424/40 |
| 6,199,557 B1 | 3/2001 | Laughlin | |

FOREIGN PATENT DOCUMENTS

| WO | WO 0109000 | 2/2001 |
|---|---|---|
| WO | WO 0112137 | 2/2001 |
| WO | WO 0112139 | 2/2001 |

* cited by examiner

*Primary Examiner*—Jose' G. Dees
*Assistant Examiner*—Marina Lamm
(74) *Attorney, Agent, or Firm*—Pillsbury Winthrop LLP

(57) ABSTRACT

The present invention is a method and apparatus for spraying makeup that masks imperfections in the skin including, but not limited to, freckles, tattoos, birthmarks, scars and post-laser surgery discoloration. The apparatus of the present invention is a hand-held sprayable cosmetic container containing a cosmetic composition that may be a foundation, a shimmer, a bronzer, a glitter, a self-tanning composition, a moisturizer, a toner, a lip color, an eyebrow color, a cheek color and/or an eye color. The apparatus may also be designed to deliver drugs (both prescription and over the counter medicines), deliver vitamins or other skin care compositions, to protect the skin from the sun, treat the skin after exposure to the sun, and/or provide an aromatherapy treatment.

21 Claims, 4 Drawing Sheets

FIGURE 3

| Component | Percent Composition |
|---|---|
| Water | 5.0 – 70.0 |
| Electrolyte | 0.1 – 3.0 |
| Cycolmethicone and dimethicone copolyol compound | 1.0 – 20.0 |
| Polygleyceryl-4 oleate and peg-8 propylene glycol cocoate compound | 0.5 – 10.0 |
| Quaternium-18 hectorite, cyclomethicone, and propylene carbonate compound | 0.5 – 10.0 |
| C12-15 Alkyl benzoate and micronized titanium dioxide compound | 1.0 – 20.0 |
| Synthetic Wax | 0.1 – 5.0 |
| Cyclomethicone | 0.5 – 50.0 |
| Titanium Dioxide and Iron Oxides | 3.0 – 20.0 |
| Botanicals | 0.0 – 10.0 |
| Preservatives | QS |
|  |  |
| OPTIONAL COMPONENTS: |  |
| Panthenol | 0.0 – 5.0 |
| Di Propylene Glycol | 0.0 – 10.0 |
| Tocopheryl Acetate | 0.0 – 5.0 |
| Retinyl Palmitate | 0.0 – 5.0 |
| Talc | 0.0 – 15.0 |
| Silica Silylate | 0.0 – 3.0 |
|  |  |
| TOTAL: | 100 % |

FIGURE 4

| Component | Percent Composition |
|---|---|
| Water | 35 |
| Sodium Chloride | 0.5 |
| Panthenol | 0.5 |
| Di Propylene glycol | 4 |
| Tocopheryl acetate | 0.1 |
| Retinyl palmitate | 0.1 |
| Cycolmethicone and dimethicone copolyol compound | 5 |
| Polygleyceryl-4 oleate and Peg-8 propylene glycol cocolate compound | 5 |
| Quaternium-18 hectorite, cyclomethicone, and propylene Carbonate compound | 1.5 |
| C12-15 alkyl benzoate and micronized titanium dioxide compound | 8.0 |
| Synthetic Wax | 1.2 |
| Cyclomethicone | 23.15 |
| Talc | 6.5 |
| Silica Silylate | 0.5 |
| Titanium Dioxide and Iron Oxides | 8.4 |
| Preservatives | QS |
| TOTAL: | 100 % |

SPRAYABLE BEAUTIFYING COMPOSITION

BACKGROUND OF THE INVENTION

1. Field of the Invention

This invention relates to the application of beautifying products, and more particularly to the spray application of specific products to a person's skin to conceal imperfections and accentuate natural features.

2. Discussion of the Related Art

Millions of people apply makeup to their skin and face daily. This makeup may be applied to cover defects in the skin, to conceal variations in color, to hide scars or blemishes, or to accent certain of the wearer's features. This process of concealing imperfections and accentuating wearers' features serves to increase wearers' self-confidence, thereby facilitating social interactions and increasing their quality of life.

Application of makeup is typically a multi-step process. The wearer may first apply a foundation primer to smooth out irregularities in the skin to provide a more even or poreless look. The wearer then applies foundation to provide an even skin color. This may then be followed by lighter "concealers" that are typically used to cover darker blemishes, pimples, freckles, scars and the dark circles that appear around the eyes.

Once the wearer has applied a sufficient amount of such foundational or concealing makeup, he or she may then choose to apply additional makeup. Such makeup may include eye shadow, blush, eyeliner and/or mascara. Eye shadow is typically applied to the eyelid and the area between the eye and the eyebrow. Blush is typically applied to the face in the cheekbone area. Such eye shadows and blush are available in a wide variety of colors. The user selects the colors based on personal preference and a "look" which is sought to be achieved. The user may also apply lip liner, and lipstick in a variety of colors.

Once the blush has been applied to the selected areas, powder may be applied in the same areas in which makeup was applied to set the makeup and to prevent it from smearing and to provide a longer wear.

Each of the various forms of makeup is applied with specialized tools. For example, it is common to apply the makeup by hand, from tubes, with brushes, sponges, or with cosmetic pencils. However, the application of the makeup by hand leads to human error. For example, if one applied foundation with a sponge, they would have to be careful to ensure that the foundation was evenly applied, and appropriately blended in with the surrounding skin. They would also have to ensure that no streaking or stroke marks showed. Such marks are readily formed as the composition is spread across the skin. Additional care must also be taken if there are any significant irregularities in the skin. The same issues also arise with eye shadow, or with the use of blended colors to achieve a certain color or look.

In order to achieve a color or a look that will last all day, the wearer typically is forced to apply more makeup than is desired in the morning. This allows a portion of the makeup to wear off throughout the day, without forcing the user to reapply the products. If makeup had a longer wearing-life, then the user would be able to apply a smaller amount and still have the effects of makeup later in the day. That is, if the makeup did not wear off, the user would only have to apply that amount of makeup that is necessary to achieve a certain look. Over-application, which is necessary to have the appearance of wearing makeup throughout the entire day without reapplication, would be unnecessary.

A common problem with many types of makeup is that it is detrimental to the skin. Many types of makeup have a tendency to clog the skin's pores, and facilitate the formation of pimples. Additionally components of the makeup, as well as the makeup removers that are necessary with many non-water-based cosmetics, tend to remove the skin's natural moisturizers and dry the skin.

Another problem with traditional makeup is that it is not suitable for those who have recently undergone cosmetic surgery. First, foundation does not adhere to skin that has been recently exposed to a laser procedure. This makes it very difficult to apply and allows the foundation to wear/brush off too easily. Since the foundation does not adhere to the skin, it separates during application. That is, it will not form a continuous coating over the skin. The resulting look after application is very patchy. Additionally, the pulling and/or tugging on the skin that is associated with attempts to apply makeup smoothly is detrimental to healing or damaged skin. Lastly, common ingredients found in foundations counteract the long-term results of the surgical procedure by drying the skin and causing new wrinkles. This problem in compounded by the fact that most consumers apply make-up products incorrectly, thereby causing premature aging of the skin.

It is known in the art to apply airbrush makeup. See for example U.S. Pat. No. 4,742,963, entitled Aerosol Airbrush, and U.S. Pat. No. 4,309,119, entitled Applicator Device for Cosmetic Preparations. However, such devices are generally only suitable for spraying water-soluble compounds. Such compounds are not water resistant, and tend to rub or wear off easily. Additionally, the complexity of these devices leads to a corresponding high cost for the devices.

Personal makeup that may be applied by the user evenly, quickly and accurately is desired. A personal, sprayable applicator capable of accomplish the above would significantly facilitate the application of makeup. It would also allow those who have recently undergone cosmetic surgery to cover up the redness and scars that are associate with cosmetic surgery through even application of a light coating. It would also reduce the need to over-apply makeup.

BRIEF DESCRIPTION OF THE DRAWINGS

FIG. 3 provides a chart detailing ranges of components of a composition that is part of one embodiment of the present invention; and FIG. 4 provides a chart detailing components of a composition that is part of one embodiment of the present invention.

DETAILED DESCRIPTION

Figure 1:
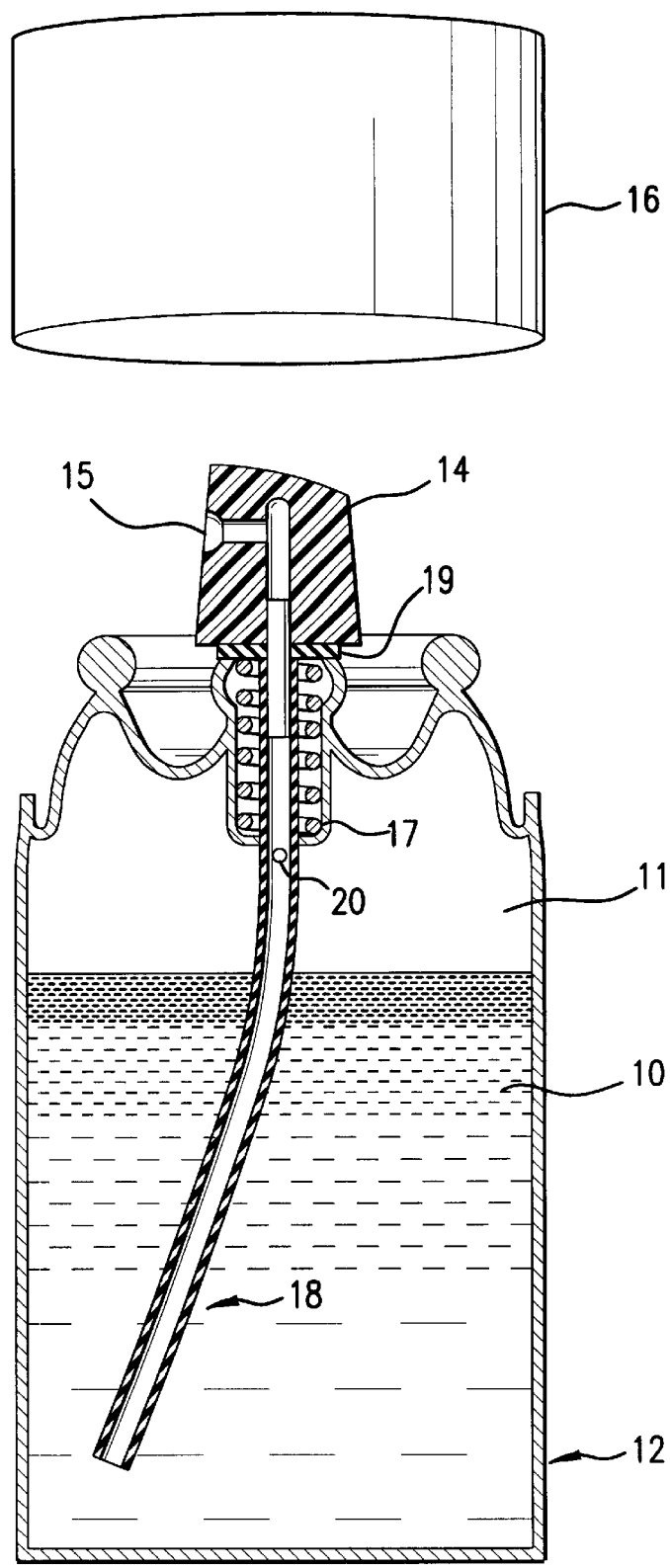
FIG. 1 illustrates a cross-section of a sprayable applicator according to one embodiment of the present invention.

The present invention is a method and apparatus for spraying makeup that masks imperfections in the skin including, but not limited to, freckles, tattoos, birthmarks, scars and post-laser surgery discoloration. The apparatus of the present invention allows for the easy application of makeup that does not require blending, stretching of the kin, or pulling or tugging at the skin. This results in less irritation to the skin. The uniform distribution of the makeup of the present invention minimizes the amount of makeup applied, yet maximized the benefits which may be achieved from such application. The apparatus of the present invention is a hand-held sprayable cosmetic container containing a cosmetic composition. Such cosmetic may be designed to be a foundation, a shimmer, a bronzer, a glitter, a self-tanning composition, a moisturizer, a toner, a lip color, an eyebrow color, a cheek color and/or an eye color. The cosmetic may also be designed to deliver drugs (both prescription and over the counter medicines), deliver vitamins or other skin care compositions, to protect the skin from the sun, treat the skin after exposure to the sun, and/or provide an aromatherapy treatment. Drugs that may be delivered to the skin in this manner may include, but are not limited to, acne medicine and alpha hydroxy acids.

The composition included within the sprayable container according to one embodiment of the present invention provides numerous beneficial effects. It moisturizes and conditions the skin, yet provides long wear and coverage. Once dry, the composition of the present invention will not smudge or rub off onto clothing. However, the composition is readily removeable with soap and water. Additionally, the composition may be designed to provide SPF protection from the sun's harmful rays.

The sprayable aspect of the present invention results in the application of makeup in fewer steps and accessories associated with the application. Since the degree of coverage may be varied by altering the length of spray time or number of spray strokes, there is no need for a primer or base coat. For a typical surface area, the spray time generally varies between about one second (for minimal coverage) and 10 seconds (for heavy coverage).

The method of the present invention produces a finish that easily blends with both the surrounding skin and with other makeup that was previously applied. Foundations must be carefully spread with a sponge to ensure even coverage that blends in with the surrounding skin. Blush must applied with a brush or other utensil and carefully blended to ensure that it provides the proper accent, without being obvious. In contrast, the sprayable composition of the present invention "feathers." That is, it naturally tapers during application towards the periphery of the area sprayed. The highest concentration of the composition may be found towards the center of the area sprayed. This concentration is subtly, but uniformly, reduced towards the periphery of the coverage. This feathering allows the composition to blend easily with surrounding surfaces. As such if one seeks to cover a scar, for example a scar on the underside of the forearm, it will not be possible to differentiate between the composition which is covering the scarred area and the surrounding undamaged tissue that is not covered with the composition.

The present invention is particularly useful for those who have seriously damaged their skin through accidents or surgical procedures such as cosmetic surgery. Since the present invention applies a quick-dry composition (the composition generally dries within 1–10 seconds, depending on the amount of the application to a particular area), it does not dry the skin like powdered makeup. It is especially important not to dry skin that has been recently damaged or exposed to laser or other surgical procedures. The fluid characteristic of the present invention also avoids the caked-on or "old" look that is associated with powdered makeup.

The makeup of the present invention provides a consistent coating over the skin area sprayed. This serves to conceal discoloration or imperfections in the skin, for example the discoloration of the skin (primarily redness) that is associated with laser surgery and skin damage. The spraying action allows the user to apply the makeup without brushing or rubbing the delicate and damaged skin. This is preferable to the application of foundations that are known in the art, since such foundations do not adhere to skin that has been recently exposed to a laser procedure. Application of such foundations to damaged or irritated skin involves a significant amount of effort and touching/brushing of the delicate skin. Even after this effort, the user typically ends up with a visibly patchy base.

Another benefit provided by the present invention to those users having skin damages and irritation, particularly that associated with laser surgery, is that the present invention does not have many of the drying agents that are found in the foundations and makeup known in the art, particularly those used to cover the signs of laser surgery. Such agents include high concentrations of talc and/or alcohol. For example, REVLON COLORSTAY (Revlon Consumer Products Corporation, New York, N.Y.) makeup, which is designed to be water-resistant and wear-resistant has a very high alcohol content. Drying agents such as alcohol counteract the long-term results of the surgical procedures by drying the skin and causing new wrinkles. They also serve to irritate damaged skin.

It is known in the art to use cosmetic compositions such as DERMABLEND ELITE (Flori Roberts, Inc., Chicago, Ill.) on damaged skin or laser-treated skin to conceal discoloration and scars. Such products are also used by those in the film industry. While this product will conceal the scarring, redness, or other damage, it is very thick and does not provide a subtle look. It is more aptly suited for its traditional use in film or television. However, with the advent of digital film and it sharpness and detail, this product will no longer be as suited for such use. The digital film will reveal the caked-on, aged look that traditional films did not.

A product, such as the instant invention, that provides a consistent, natural look that suitably conceals the underlying imperfections or damage would be a great improvement over DERMABLEND—both in the film industry and on damaged skin. It greatly reduces, and in some cases completely conceals, the appearance of wrinkles, redness, scars and imperfections in the skin. This provides a very finished look, regardless of whether it is shown on digital film, or viewed in person.

FIG. 1 illustrates a cross-section of a sprayable applicator according to one embodiment of the present invention. While FIG. 1 is provided as an illustration of a sprayable applicator, it should be understood by one skilled in the art that many different applicators, and nozzles, may achieve the benefits and purposes of the present invention.

As may be see in FIG. 1, a cosmetic composition 10 and propellant 11 are contained within the body of a pressurized canister 12. While the propellant as illustrated is located above the composition, it should be understood by one skilled in the art that the propellant may be partially liquid and partially gaseous. Both the liquid propellant and the gaseous propellant may mix, in varying proportions, with the composition. The propellant may be any propellant that is known in the art. By way of example, and not limitation, the propellant may be compressed air or a volatile organic compound such as isobutane.

The canister 12 is equipped with a bushing and an actuator 14 having an opening 15 through which the cosmetic composition 10 and propellant 11 may be dispensed. The cosmetic composition 10 is dispensed through nozzle 15 when a user depresses the actuator 14. A cap 16, shown separately from the apparatus for clarification purposes, may be associated with the container to protect the actuator and valve assembly and to prevent accidental dispensing of the composition. The cap 16 should be designed so at to fit securely onto canister 12. Such a cap 16 may be particularly useful, for example, if the present invention is stored or carried by the user in a bag or purse.

In one embodiment of the present invention (shown), the canister 12 is equipped with a gasket 19, a dip tube 18 and a spring 17. As the actuator 14 is activated, pressure is exerted on the spring 17, thereby causing the gasket 19 to flex. This forces the composition 10 and propellant 11 to enter the valve stem orifice 20 and to be expelled through the nozzle 15. The dip tube 18 serves to ensure that both composition and propellant are expelled during this operation.

It should be understood by one skilled in the art that the spring 17 may not be necessary if certain portions of the mechanism of the apparatus are made of rubber or other flexible material. The gasket 19 similarly may be replaced with an orifice that may be controllably opened and closed by the actuator 14.

In one embodiment of the present invention, the canister 12 is sized so that it may be easily held in a user's hand and sprayed. Specifically, the canister may be between 2 and 12 inches in length. Preferably, the canister is between 4 and 10 inches in length. Most preferably, the canister is between 5 and 8 inches in length. The canister may range in diameter from 0.5 inches to 6 inches. Most preferably, the canister is between 1 inch and 3 inches in diameter.

The spray pattern of the present invention may be varied depending on the amount of surface area to be covered may be varied by changing the size of the nozzle 15. However, the texture of the spray should not vary. That is, regardless of the area being sprayed, the spray should always resemble a directed mist. The spray pattern may be designed to cover an area having a ½-inch to 8-inch diameter, with a 2 to 5-inch diameter being preferred.

In order to protect users who apply the sprayable makeup of the present invention to the face and eye area, the present invention may include goggles. This allows the user to spray the present invention without fear of contacting the present invention with the eyes. Users wearing goggles will also be less inclined to squint or otherwise wrinkle the skin during application. Such wrinkling or creasing of the skin may lead to uneven application of the makeup of the present invention.

Such goggles are preferably primarily clear and allow for a certain amount of peripheral vision so that the user has full use of his/her eyes during use of the invention. In one embodiment of the present invention, the goggles are lightweight and crack-resistant. For example, and not by way of limitation, the goggles may be glass, plastic, or lucite. The goggles may also be worn by users wishing to take additional safety precautions when they apply embodiments of the present invention to other body parts.

Figure 2:
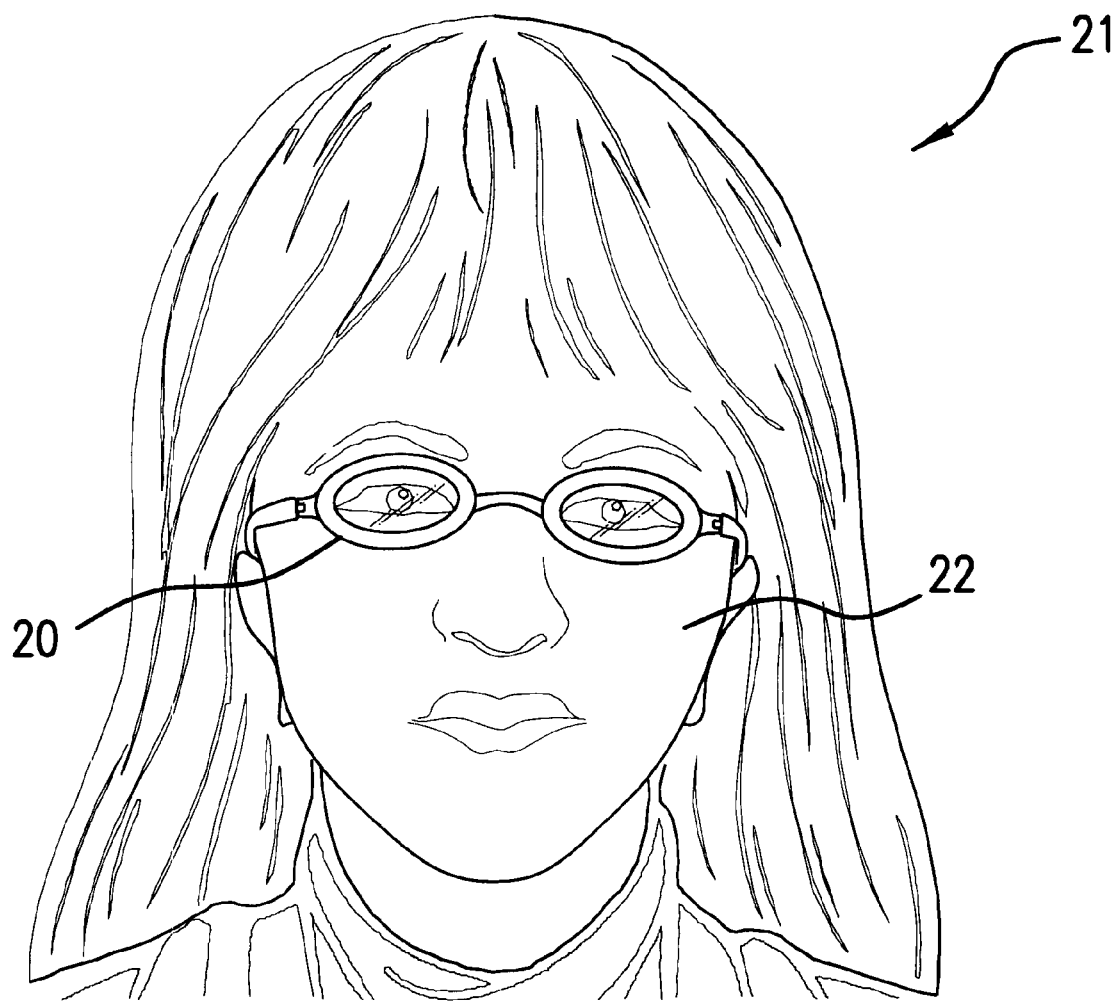
FIG. 2 provides an illustration of one embodiment of the present invention.

FIG. 2 provides an illustration of one embodiment of the present invention. As shown in FIG. 2, goggles 20 or similar eye coverings may be included as part of the present invention. The goggles 20 may be worn by the user 21 during application of the present invention to the face or eye area 22 to protect the eyes. If the user wishes to apply the method of the present invention to the eye area 22, she may briefly lift or remove the goggles to spray the eye area 22 while keeping her eyes closed.

FIG. 3 provides a chart detailing components of a composition that is part of one embodiment of the present invention. This composition is water-resistant and has a long wearing life. Water will not effect the composition's placement on the skin unless soap is also used. Alternatively, other compounds that are specifically designed to remove makeup may be used to remove the composition that is part of the present invention.

As may be seen FIG. 3, the composition may include: water; an electrolyte; a cyclomethicone and dimethicone copolyol compound; a polygleyceryl-4 oleate and peg-8 propylene glycol cocoate compound; a quaternium-18 hectorite, cyclomethicone, and propylene carbonate compound; a micronized titanium dioxide-containing compound; synthetic wax; cyclomethicone; metal oxides, preservatives and various botanicals. The composition may also optionally include panthenol, di propylene glycol, tocopheryl acetate, retinyl palmitate, talc and/or silica silylate. As noted above, talc may be detrimental to damaged, sensitive, dry or laser-treated skin. As such, its inclusion should be carefully monitored depending on the condition of the skin of the user.

The various components of the composition serve various purposes. Panthenol is a skin conditioner and moisturizer. Di propylene glycol is a humectent. The tocopheryl acetate and retinyl palmitate, vitamins E and A, are anti-oxidants and moisturizers. The cyclomethicone and dimethicone copolyol compound and polygleyceryl-4 oleate and peg-8 propylene glycol cocoate compound serve as emulsifiers. The quaternium-18 hectorite, cyclomethicone and propylene carbonate compound and the silica silylate are suspending agents. The micronized titanium dioxide-containing compound may be any as is known in the art including, but not limited to: a C12–15 Alkyl Benzoate and titanium dioxide compound or composition; a cyclomethicone and micronized titanium dioxide compound or composition; a water and micronized titanium dioxide compound or composition; a ethyl hexyl palmitate and micronized titanium dioxide compound or composition; a caprilic/capric triglyceride and mineral oil and micronized titanium dioxide compound or composition; and/or a caprilic/capric triglyceride and micronized titanium dioxide compound or composition. The titanium dioxide percent composition in C1215 alkyl benzoate and titanium dioxide compound is between 2 and 3 percent by weight, typically approximately 2.3%.

The electrolyte serves to enhance shelf life stability and enhance the composition's ability to withstand freeze-thaw cycling. Any suitable electrolyte as is known in the art may be used including, but not limited to, sodium chloride, sodium citrate, magnesium sulfate, sodium borate or aluminum chlorohydrate. The metal oxides may be any colorant that is known in the art including, but not limited to, titanium dioxide and iron oxides. Talc is used as a filler, and may be used to provide the makeup with a desirable feel. "Botanicals" include, but are not limited to, aloe and chamomile extracts.

FIG. 4 provides a formula for preparing the composition according to one embodiment of the present invention.

This composition provides the disclosed benefits, and more, by coating the skin to provide a poreless appearance. This is accomplished through the creation of a thin and extremely uniform film across the surface of the skin. The film in generated in large part by a synergistic effect that is seen between the synthetic wax and the micronized titanium dioxide. The synthetic wax may be added to the composition in dry or liquid form. It is water-resistant and assists in the drying of the solvent.

Titanium dioxide is a white opaque pigment that provides coverage and color to the composition. The typical particle size of the titanium dioxide, which has a platelet shape, is typically larger than one micron, and usually in the range of 5–15 microns. Micronized titanium dioxide, in contrast, has a typical size of between 0.15 and 0.3 angstroms. This significant change in size does not change the shape of the titanium dioxide. The titanium dioxide of the present invention provides an additional benefit—sun protection. The titanium dioxide of the present invention may provide a SPF of 18–24.

The synthetic wax acts in concert with the micronized titanium dioxide to produce a thin and exceedingly uniform film of platelets on the surface of the skin. This film is water-resistant and resists forces which would cause makeup that is known in the art to rub off. That is, the film provides a wear-proof characteristic to the composition. This resistance to frictional forces which cause other makeup to rub off is due in part to the thinness of the film. Since the particles are very close to, or in direct contact with, the skin the composition has an increased tendency to resist removal.

The wax/titanium dioxide film may be set by a volatile silicone, such as cyclomethicone. This further serves to increase the wear time of the composition.

The formation of the composition according to one embodiment of the present invention is a multi-step process that may be performed at room temperature. Distinct water and oil phases are first prepared and individually mixed. The water phase may include water, an electrolyte, panthenol, di propylene glycol and preservatives. The oil phase may include: tocopheryl acetate; retinyl palmitate; the cyclomethicone and dimethicone copolyol compound; the polygleycery-4 oleate and peg-8 propylene glycol cocoate compound; the quaternium-18 hectorite, cyclomethicone and propylene carbonate compound; the titanium dioxide compound; synthetic wax; and cyclomethicone. It should be noted that some of the composition constituents noted as optional have been included in this description of the formation of the composition. This is for ease of explanation purposes only.

The water phase should be mixed until uniform; the oil phase may be mixed until just blended. A third phase, termed the pigmented phase for ease of explanation, is then added to the oil phase and mixed until the pigmented oil phase is uniform in texture and appearance. This mixing may be performed by any means that is known in the art. The pigmented phase may include talc, silica silylate, the metal oxides, and preservatives.

The pigmented oil phase is then placed in the hopper of an apparatus having propeller mixing blades, such as a colloid mill or hydroshear, and further blended or ground until a sample of the phase examined between glass slides shows no color spots. The blending in one embodiment of the present invention may be performed at a gap setting of between 4 and 6 microns.

After the pigmented oil phase has achieved sufficient consistency as described above, the water phase may be mixed with the pigmented oil phase. Such mixing must be performed by slowly adding the water phase to the pigmented oil phase. In the lab, this is achieved by adding the water on a drop-by-drop basis. When making the composition on a larger scale, the addition rate may be increased to a slow trickle. For example, approximately 1 kilogram per hour of the water phase may be added to the oil phase when making a 500-kilogram batch of the composition. This combination of the pigmented oil and water phases should be performed with constant mixing. Due to the slow mixing of the two phases, this may take a significant amount of time to completely combine the two phases. After the two phases have been combined into one, the combination is then mixed and run 1 pass through the colloid mill having a gap setting of between 4 and 6 microns.

The resulting composition according to one embodiment of the present invention is approximately 35–45% derived from the water phase, and 55–65% derived from the pigmented oil phase. However, depending on the desired characteristics of the composition, alternate embodiments may have percentage compositions that vary from this embodiment.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of concealing imperfections and accentuating a person's natural features, the method consisting essentially of:

pointing a nozzle of a pressurized container towards an area of skin to be coated, wherein the pressurized container holds a cosmetic composition capable of forming a thin, water-resistant coating of generally uniform thickness on the skin that tapers in thickness during application towards the periphery of the area sprayed, the composition comprised of:
  from about 5.0 to 70.0 percent by weight water;
  from about 0.1 to 3.0 percent by weight of an electrolyte;
  from about 1.0 to about 20.0 percent by weight of a cycolmethicone and dimethicone copolyol compound;
  from about 0.5 to about 10.0 percent by weight of a polygleyceryl-4 oleate and peg-8 propylene glycol cocoate compound;
  from about 1.0 to about 20.0 percent by weight of a micronized titanium dioxide-containing compound;
  from about 0.1 to about 5.0 percent by weight of synthetic wax, wherein the synthetic wax and the micronized titanium dioxide-containing compound exhibit a synergistic film-forming effect;
  from about 0.5 to about 50.0 percent by weight of cyclomethicone;
  from about 3.0 to about 20.0 percent by weight of a metal oxide; and
  a preservative, wherein the composition does not dry damaged skin, and further wherein the composition will adhere to laser-treated skin, and spraying the cosmetic composition on skin such that a uniform, thin coating which blends with the surrounding skin is formed on the surface of the skin.

2. The method according to claim 1, wherein the electrolyte is selected from the group consisting of: sodium chloride, sodium citrate, magnesium sulfate, sodium borate and aluminum chrorohydrate.

3. The method according to claim 1, wherein the cosmetic composition further includes alpha hydroxy acid.

4. The method according to claim 1, wherein the cosmetic composition further includes from about 0.1 to about 3.0 percent by weight panthenol.

5. The method according to claim 1, wherein the cosmetic composition further includes from about 0.1 to about 10.0 percent by weight di propylene glycol.

6. The method according to claim 1, wherein the cosmetic composition further includes from about 0.01 to about 5.0 percent by weight tocopheryl acetate.

7. The method according to claim 1, wherein the cosmetic composition further includes from about 0.01 to about 5.0 percent by weight retinyl palmitate.

8. The method according to claim 1, wherein the cosmetic composition further includes from about 0.5 to about 15.0 percent by weight talc.

9. The method according to claim 1, wherein the cosmetic composition further includes from about 0.05 to about 3.0 percent by weight silica silylate.

10. The method according to claim 1, wherein the nozzle is pointed at a face.

11. The method according to claim 1, wherein the nozzle is pointed at a body part of a user.

12. A sprayable system for applying a thin layer of particularized cosmetic, the system comprising:
   a pressurized container;
   an actuator;
   a propellant; and
   a cosmetic composition, wherein the composition will not dry damaged skin, and further wherein the composition will adhere to laser-treated skin, the composition composed of:
      from about 5.0 to 70.0 percent by weight water;
      from about 0.1 to 3.0 percent by weight of an electrolyte;
      from about 1.0 to about 20.0 percent by weight of a cycolmethicone and dimethicone copolyol compound;
      from about 0.5 to about 10.0 percent by weight of a polygleyceryl-4 oleate and peg-8 propylene glycol cocoate compound;
      from about 1.0 to about 20.0 percent by weight of a micronized titanium dioxide-containing compound;
      about 0.1 to about 5.0 percent by weight of synthetic wax, wherein the synthetic wax and the micronized titanium dioxide-containing compound exhibit a synergistic film-forming effect;
      from about 0.5 to about 50.0 percent by weight of cyclomethicone;
      from about 3.0 to about 20.0 percent by weight of a metal oxide; and
      a preservative,
   wherein the composition does not dry damaged skin, and further wherein the composition will adhere to laser-treated skin, and further wherein the system provides a thin, water-resistant coating of uniform thickness on the skin that naturally tapers during application towards the periphery of the area sprayed.

13. The cosmetic system according to claim 12, the composition further including alpha hydroxy acid.

14. The cosmetic system according to claim 12, the composition further including from about 0.1 to about 3.0 percent by weight panthenol.

15. The cosmetic system according to claim 12, the composition further including from about 0.1 to about 10.0 percent by weight di propylene glycol.

16. The cosmetic system according to claim 12, the composition further including from about 0.01 to about 5.0 percent by weight tocopheryl acetate.

17. The cosmetic system according to claim 12, the composition further including from about 0.01 to about 5.0 percent by weight retinyl palmitate.

18. The cosmetic system according to claim 12, the composition further including from about 0.5 to about 15.0 percent by weight talc.

19. The cosmetic system according to claim 12, the composition further including from about 0.05 to about 3.0 percent by weight silica silylate.

20. The method as in claim 1, the composition further comprising from about 0.5 to about 10.0 percent by weight of a quaternium-18 hectorite, cyclomethicone, and propylene carbonate compound.

21. The system as in claim 12, the composition further comprising from about 0.5 to about 10.0 percent by weight of a quaternium-18 hectorite, cyclomethicone, and propylene carbonate compound.

* * * * *